(12) United States Patent
Chen

(10) Patent No.: US 12,161,388 B2
(45) Date of Patent: Dec. 10, 2024

(54) ELECTRIC PULSE ABLATOGRAPH FOR ENDOSCOPE

(71) Applicant: Hangzhou Ready Biological Technology Co., Ltd, Zhejiang (CN)

(72) Inventor: Yonggang Chen, Zhejiang (CN)

(73) Assignee: HANGZHOU READY BIOLOGICAL TECHNOLOGY CO., LTD, Zhejiang (CN)

( * ) Notice: Subject to any disclaimer, the term of this patent is extended or adjusted under 35 U.S.C. 154(b) by 685 days.

(21) Appl. No.: 17/600,473

(22) PCT Filed: Aug. 19, 2019

(86) PCT No.: PCT/CN2019/101290
§ 371 (c)(1),
(2) Date: Sep. 30, 2021

(87) PCT Pub. No.: WO2020/232851
PCT Pub. Date: Nov. 26, 2020

(65) Prior Publication Data
US 2022/0175442 A1   Jun. 9, 2022

(30) Foreign Application Priority Data
May 18, 2019 (CN) .......................... 201910415844.5

(51) Int. Cl.
*A61B 18/14* (2006.01)
*A61B 17/00* (2006.01)
(Continued)

(52) U.S. Cl.
CPC ........ *A61B 18/1477* (2013.01); *A61B 1/0008* (2013.01); *A61B 2017/00398* (2013.01);
(Continued)

(58) Field of Classification Search
None
See application file for complete search history.

(56) References Cited

U.S. PATENT DOCUMENTS 5,976,129 A * 11/1999 Desai ................ A61B 18/1477
606/42
2017/0360502 A1   12/2017 Osypka
2018/0028267 A1 *  2/2018 Onik ...................... A61B 5/055

FOREIGN PATENT DOCUMENTS

CN   101563040 A   10/2007
CN   103251452 A   8/2013
(Continued)

*Primary Examiner* — Linda C Dvorak
*Assistant Examiner* — Nicholas S Borsch
(74) *Attorney, Agent, or Firm* — Muncy, Geissler, Olds & Lowe, P.C.

(57) ABSTRACT

The present application relates to the technical field of pulse ablation, in particular to an electric pulse ablatograph for an endoscope, which includes: an electrode assembly including a central electrode and a cylindrical electrode and configured to pass through a working channel of the endoscope into a body and transmit a pulse to tissues in use; a pulse waveform generator coupled to the electrode assembly and configured to transmit pulse voltage to the electrode assembly; an electrode driving device configured to drive the central electrode and the cylindrical electrode; a parameter input device configured to configure coordinate information of an ablation region; and a control device in signal connection with the parameter input device and in control connection with the electrode driving device. The control device respectively controls the displacement of the central electrode and cylindrical electrode according to preset coordinate information through the electrode driving device; when a discharging end of the electrode assembly reaches a preset position, the control device controls the pulse waveform generator to be connected with the electrode assembly. A (Continued)

natural channel in a human body is used to deliver the electrode to a complex area of the human body for ablation, thus decreasing the trauma to the human body.

9 Claims, 8 Drawing Sheets

(51) Int. Cl.
    *A61B 18/00*     (2006.01)
    *A61B 1/00*     (2006.01)

(52) U.S. Cl.
    CPC ............... *A61B 2018/00083* (2013.01); *A61B 2018/00577* (2013.01); *A61B 2018/00702* (2013.01); *A61B 2018/00982* (2013.01); *A61B 2018/1405* (2013.01); *A61B 2018/1467* (2013.01); *A61B 2018/1475* (2013.01)

(56) References Cited

FOREIGN PATENT DOCUMENTS

| | | |
|---|---|---|
| CN | 108013931 A | 5/2018 |
| CN | 108272503 A | 7/2018 |
| CN | 207804370 U | 9/2018 |

\* cited by examiner

ELECTRIC PULSE ABLATOGRAPH FOR ENDOSCOPE

TECHNICAL FIELD

The present application relates to the technical field of pulse ablation, in particular to an electric pulse ablatograph for an endoscope.

BACKGROUND ART

At present, the clinical treatment of tumors is mainly radical surgical excision. But for tumors in areas such as pancreas, bile ducts and hepatic ducts with dense ducts, the trauma of cavity opening operation is large, the wound healing time is long, and the wound cannot touch water during wound healing, thus bringing inconvenience to the daily life of patients.

A medical endoscope can enter a human body through a natural channel of the human body, or through a small incision made by surgery. Through the endoscope for examination, the human body is less traumatic. Some endoscopes even have working channels, which can carry special apparatuses and have many functions such as lighting, surgery, flushing and suction. This kind of endoscopes with working channels undoubtedly provides the possibility for the application of electric pulse ablation technology.

In addition, the current ablation apparatus using double needle parallel electrodes has the problems that the distance between the two electrodes is fixed, the size of the generated electric field is fixed, and the size of the electric field cannot be adjusted with the ablation cross section of the tumor in the process of electrode advancement, such that the multiple operations are needed to achieve the effect and the ablation effect is poor.

Therefore, the working personnel in this field urgently need a device that can deliver the electrodes of the electric pulse ablation apparatus into the body with the help of the endoscope, can adjust the size of the electric field and can realize accurate treatment, so as to reduce the trauma to the human body when treating tumors in areas such as pancreas, bile ducts and hepatic ducts with dense ducts.

SUMMARY

The technical problem to be solved by the present application is to overcome the defects in the prior art, and provide an electric pulse ablatograph for an endoscope, which can precisely control the entry of electrodes, generate a variable electric field, release energy evenly and decrease the trauma to the human body.

In order to achieve the purpose, the present application is implemented through the following technical solution: an electric pulse ablatograph for an endoscope, including: an electrode assembly including a central electrode and a cylindrical electrode and configured to pass through a working channel of the endoscope into a body and transmit a pulse to tissues in use; a pulse waveform generator coupled to the electrode assembly and configured to transmit pulse voltage to the electrode assembly; an electrode driving device configured to drive the central electrode and the cylindrical electrode; a parameter input device configured to configure coordinate information of an ablation region; and a control device in signal connection with the parameter input device and in control connection with the electrode driving device, wherein the control device respectively controls the displacement of the central electrode and cylindrical electrode according to preset coordinate information through the electrode driving device; when a discharging end of the electrode assembly reaches a preset position, the control device controls the pulse waveform generator to be connected with the electrode assembly; when the electrode assembly is connected with the pulse waveform generator, an ablation electric field is generated between the discharging end of the central electrode and the cylindrical electrode, and the size or radius of the ablation electric field is positively correlated to the distance between the discharging end of the central electrode and the cylindrical electrode; the ablation electric field forms the ablation region after moving according to a preset path, and the ablation region is elliptical; the electrode assembly is a layered structure, an outer side of the central electrode is plated with an insulating layer, and the part of the central electrode covered with the insulating layer is exposed out of the cylindrical electrode; the central electrode is retractably provided in the cylindrical electrode, and the cylindrical electrode is retractably provided in an outer sheath tube; the electrode driving device includes a fixed part and a displacement part capable of producing a relative displacement, a first electric actuator provided on the fixed part and configured to drive the cylindrical electrode, and a second electric actuator provided on the displacement part and configured to drive the central electrode; the control device adjusts the size of the ablation electric field by changing the displacement difference between the cylindrical electrode and the central electrode.

In this way, on the one hand, the electrode assembly is delivered to a complex area of the human body for ablation through a natural channel of the human body, so as to decrease the trauma to the human body; on the other hand, the control device controls the central electrode and the cylindrical electrode to produce a displacement difference during movement, and the size of the electric field is adjusted through the displacement difference, such that the size of the electric field can be adjusted with the (tumor) ablation cross section to ensure that the electric field energy on the unit area of the cross section at different positions is similar, the treatment effect is good, and the treatment times are decreased.

As a further alternative solution of the present application, a front end of the fixed part is abutted with an inlet end of the working channel of the endoscope, the electrode assembly is placed in the working channel of the endoscope, a tail end of the outer sheath tube is fixedly connected with the fixed part, a tail end of the cylindrical electrode is fixedly connected with the displacement part, and the first electric actuator drives the displacement part to drive the cylindrical electrode to extend and retract in the outer sheath tube, As a further alternative solution of the present application, the fixed part is in a needle tube shape, and a front end of the fixed part is provided with an interface for abutting the endoscope; the outer sheath tube is provided on the fixed part in a penetrating manner, one end of the outer sheath tube extends into the endoscope through the interface, and a tail end of the outer sheath tube and the fixed part are fastened through a cap in interference fit; the displacement part is cylindrical, sleeves the fixed part and is slidably provided relative to the fixed part in an axial direction; a tail end of the displacement part is provided with a cylindrical electrode tube seat for fixing the cylindrical electrode.

As a further alternative solution of the present application, the first driving device and/or the second driving device includes a motor screw-nut mechanism or a linear motor.

As a further alternative solution of the present application, the first driving mechanism is a motor screw-nut mechanism and includes a first motor, a screw and a nut; the first motor is fixedly provided on the fixed part, the nut sleeves the screw and is fixedly connected with the displacement part, and the first motor is in drive connection with the nut through the screw; the control device controls the extending and retraction displacement and speed of the cylindrical electrode in the outer sheath tube by controlling the number of turns and the revolving speed of the first motor.

As a further alternative solution of the present application, the second driving mechanism is a linear motor and includes a second motor and a push rod; the second motor is fixedly provided on the displacement part, the second motor is in drive connection with one end of the push rod, and the other end of the push rod is connected with the central electrode through a connector; the control device controls the extending and retraction displacement and speed of the central electrode in the cylindrical electrode by controlling the number of turns and the revolving speed of the second motor.

As a further alternative solution of the present application, the parameter input device includes an ultrasonic probe for detecting a tissue boundary and an electrode position, and a touch screen for imaging; the coordinate information of the ablation region includes a long axis and a short axis for determining the size of the ablation region, and the long axis and the short axis are determined by clicking an image on the touch screen.

As a further alternative solution of the present application, the central electrode includes a working section at an end and a conducting section at a rear end for conducting voltage; during working, a pulse electric field is generated between the working section and the cylindrical electrode; the insulating layer is plated outside the conducting section.

As a further alternative solution of the present application, the central electrode is tubular and is hollow inside to form a medicine delivery channel for delivering medicine; a front end of the working section is provided with a sharp part.

To sum up, the present application has the following beneficial effects: on the one hand, the electrode assembly is delivered to a complex area of the human body for ablation through a natural channel of the human body, so as to decrease the trauma to the human body; on the other hand, the control device controls the central electrode and the cylindrical electrode to produce a displacement difference during movement, and the size of the electric field is adjusted through the displacement difference, such that the size of the electric field can be adjusted with the (tumor) ablation cross section to ensure that the electric field energy on the unit area of the cross section at different positions is similar, the treatment effect is good, and the treatment times are decreased.

Figure 1:
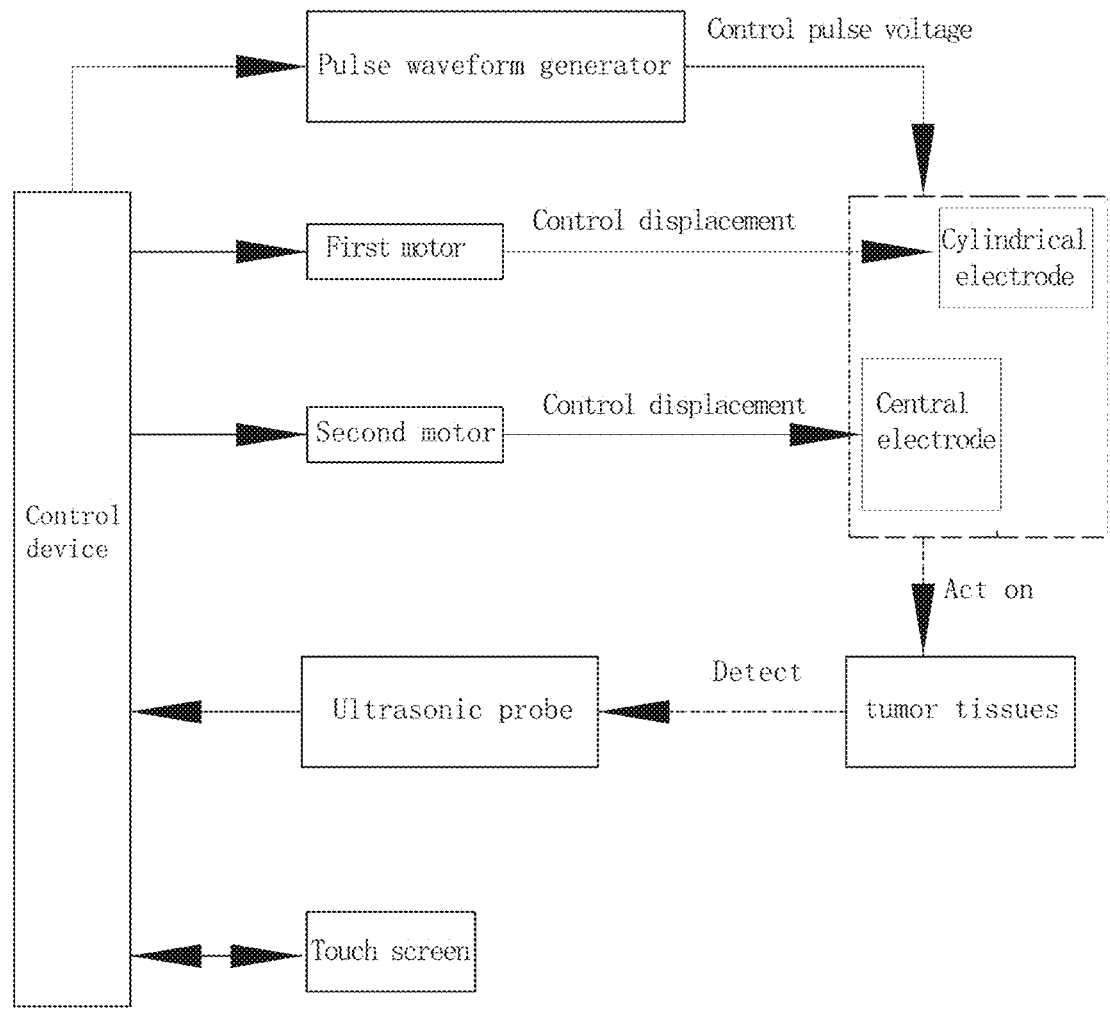
FIG. 1 illustrates a schematic diagram of an ablatograph.
Figure 2:
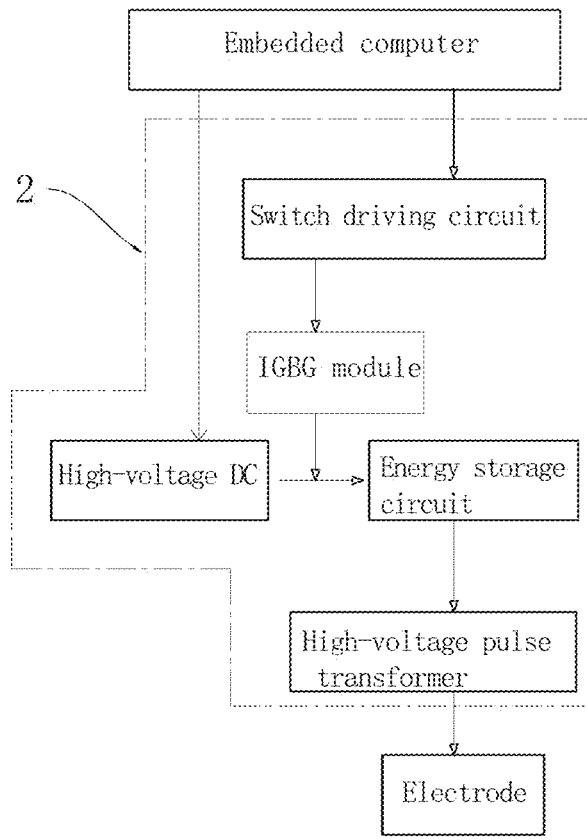
FIG. 2 illustrates a schematic circuit diagram of a pulse waveform generator.
Figure 3:
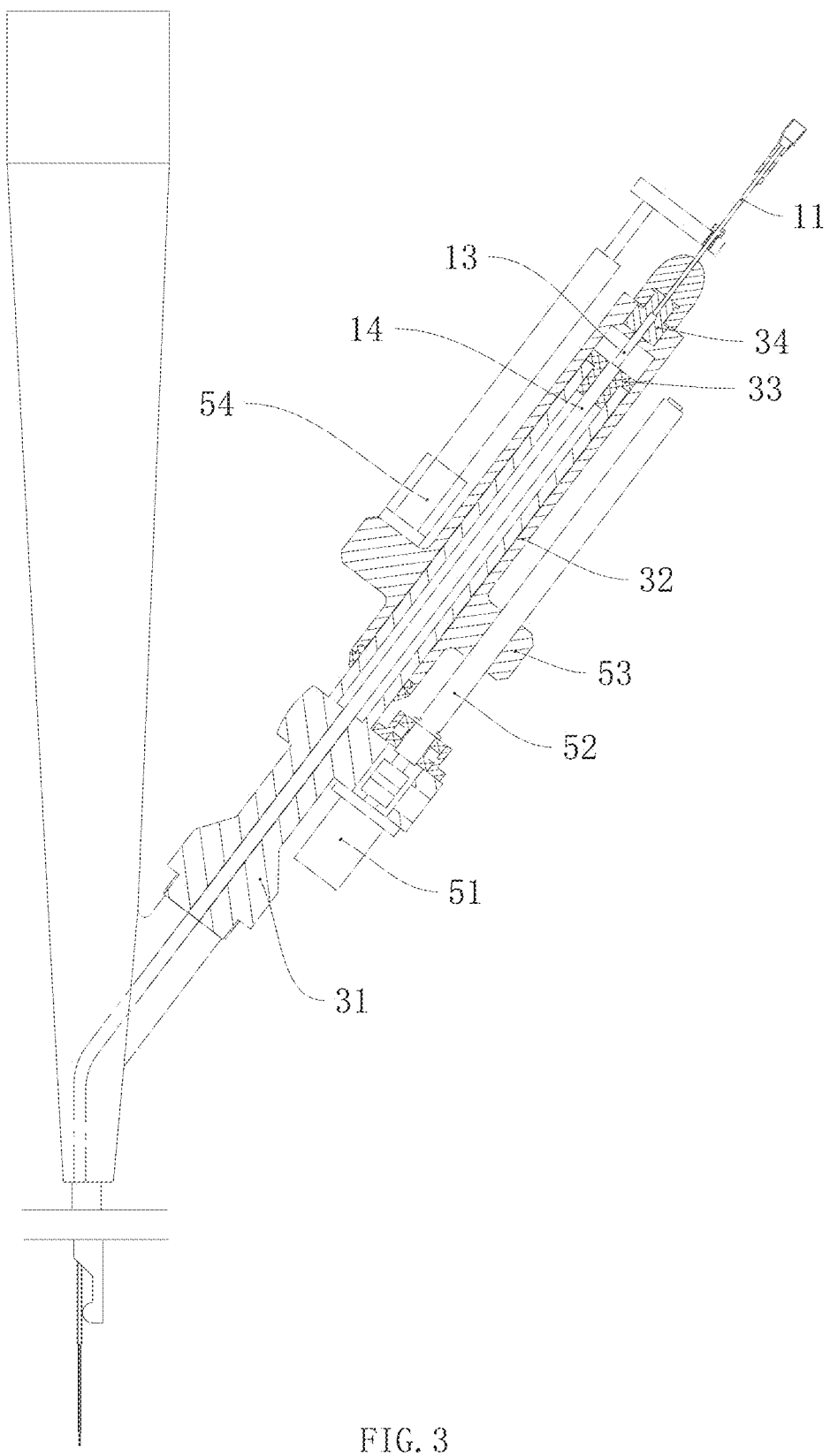
FIG. 3 illustrates a cross-sectional view of an electrode driving device.
Figure 4:
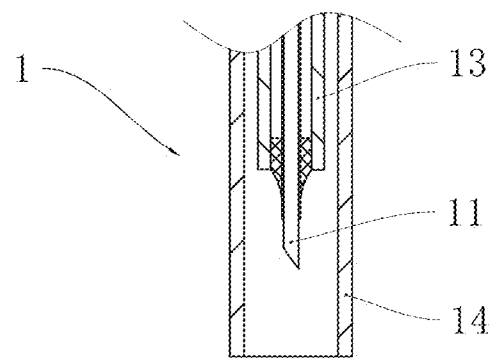
FIG. 4 illustrates a position status view when an electrode assembly reaches a position near a target.
Figure 4:
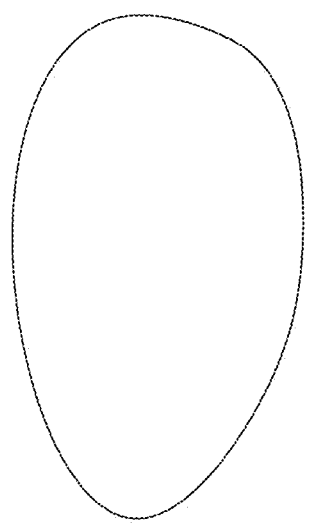
Figure 5:
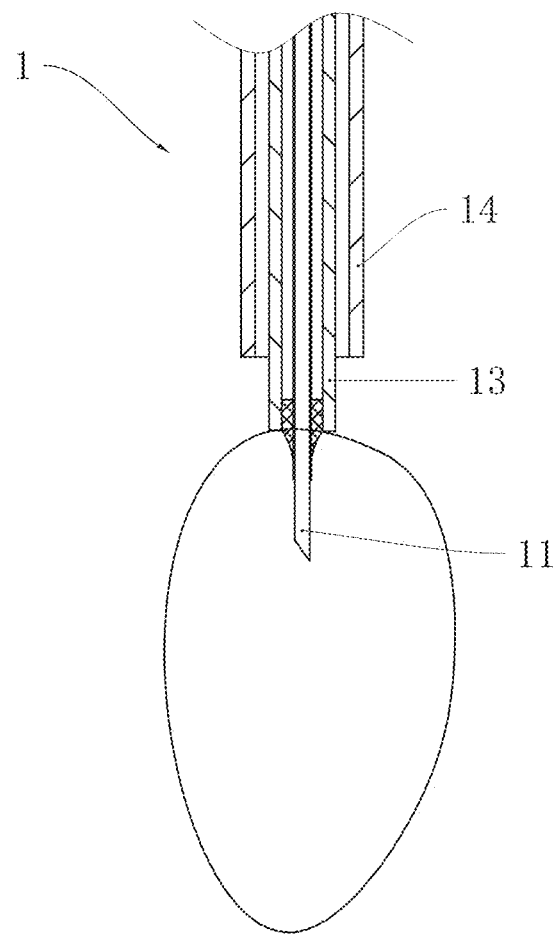
FIG. 5 illustrates a position status view when a central electrode pierces a target.
Figure 6:
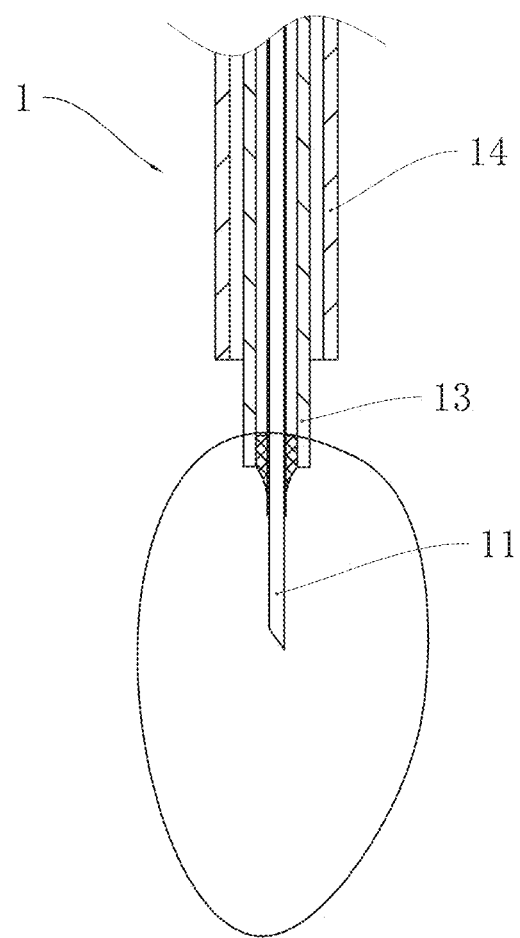
FIG. 6 illustrates a position status view when a central electrode and a cylindrical electrode are located at a central portion of a target.
Figure 7:
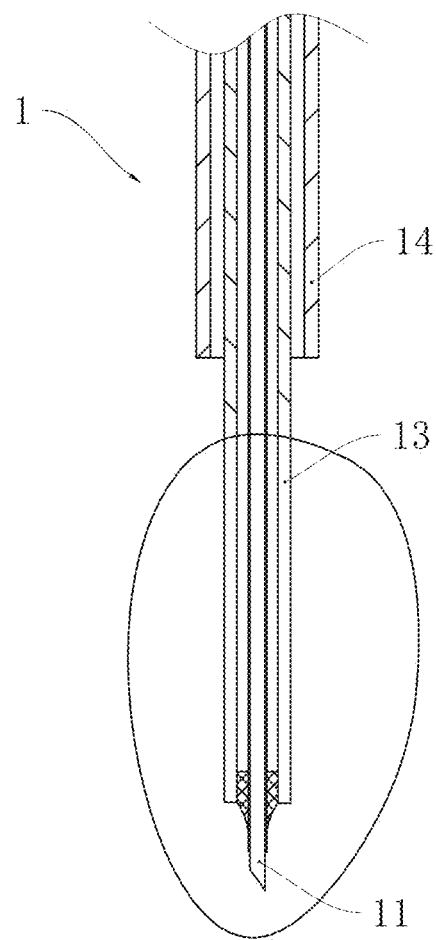
FIG. 7 illustrates a position status view when a central electrode and a cylindrical electrode reach a tail end of a target.

In the drawings: 1—electrode assembly; 11—central electrode; 13—cylindrical electrode; 14—outer sheath tube; 2—pulse waveform generator; 31—fixed part; 32—displacement part; 33—cap; 34—tube seat; 51—first motor; 52—screw; 53—nut; 54—second motor; 55—push rod; 56—connector.

DESCRIPTION OF THE EMBODIMENTS

The present application will be further described below in detail with reference to the drawings.

The embodiments are only used for explaining the present application instead of limiting the present application. Those skilled in the art may make modifications to the embodiments according to the needs without contributing any inventive labor after reading the description, which, however, are protected by the Patent Law as long as the modifications fall within the scope of the claims of the present application.

FIG. 1, FIG. 2, FIG. 3 and FIG. 4 illustrate an electric pulse ablatograph for an endoscope, which mainly includes an electrode assembly 1, a pulse waveform generator 2, an electrode driving device, a parameter input device and a control device.

The electrode assembly 1 includes a central electrode 11 and a cylindrical electrode 13 and is configured to pass through a working channel of the endoscope into a body and transmit a pulse to tissues in use.

In this embodiment, the electrode assembly 1 is a layered structure, and the central electrode 11 includes a working section at an end and a conducting section at a rear end for conducting voltage. During working, a pulse electric field is generated between the working section and the cylindrical electrode 13. The insulating layer is plated outside the conducting section. The working section of the central electrode 11 covered with the insulating layer is exposed out of the cylindrical electrode 13. The central electrode 11 is retractably provided in the cylindrical electrode 13, and the cylindrical electrode 13 is retractably provided in an outer sheath tube 14.

In order to facilitate timely medicine application after ablation, the central electrode 11 is tubular and is hollow inside to form a medicine delivery channel for delivering medicine, and a front end of the working section is provided with a sharp part to facilitate piercing tissues.

The pulse waveform generator 2 is coupled to the electrode assembly 1 and configured to transmit pulse voltage to the electrode assembly 1. The working principle of the pulse waveform generator 2 is the prior art, which will not be described here in detail one by one. For the schematic circuit diagram and the working principle, please refer to Chinese application No. 2019102479418.

The electrode driving device is fixedly provided on the endoscope and is configured to drive the central electrode 11 and the cylindrical electrode 13. The electrode driving device includes a fixed part 31 and a displacement part 32 capable of producing a relative displacement, a first electric actuator provided on the fixed part 31 and configured to drive the cylindrical electrode 13, and a second electric actuator provided on the displacement part 32 and configured to drive the central electrode 11.

The fixed part 31 is in a needle tube shape, and a front end of the fixed part 31 is provided with an interface for abutting the endoscope. The outer sheath tube 14 is provided on the fixed part 31 in a penetrating manner, one end of the outer sheath tube 14 extends into the endoscope through the interface, and a tail end of the outer sheath tube 14 and the fixed part 31 are fastened through a cap 33 in interference fit.

The displacement part 32 is cylindrical, sleeves the fixed part 31 and is slidably provided relative to the fixed part 31 in an axial direction. A tail end of the displacement part 32 is provided with a cylindrical electrode 13 tube seat for fixing the cylindrical electrode 13 and a cylindrical electrode 13 wiring seat.

The first driving device and/or the second driving device includes a motor screw-nut mechanism or a linear motor. In this embodiment, description is made by taking that the first driving mechanism is a motor screw-nut 53 mechanism and the second driving mechanism is a linear motor as an example.

The first driving mechanism includes a first motor 51, a screw 52 and a nut 53; the first motor 51 is fixedly provided on the fixed part 31, the nut 53 sleeves the screw 52 and is fixedly connected with the displacement part 32, the first motor 51 is in drive connection with the nut 53 through the screw 52, and the displacement part 32 is driven to drive the cylindrical electrode 13 to extend and retract in the outer sheath tube 14.

The second driving mechanism includes a second motor 54 and a push rod 55; the second motor 54 is fixedly provided on the displacement part 32, the second motor 54 is in drive connection with one end of the push rod 55, the other end of the push rod 55 is connected with the central electrode 11 through a connector 56, and the extending and retraction displacement and speed of the central electrode 11 in the cylindrical electrode 13 are controlled through the extension and retraction of the push rod 55.

The control device respectively and indirectly control the extending and retraction displacement and speed of the cylindrical electrode 13 in the outer sheath tube 14 and of the central electrode 11 in the cylindrical electrode 13 by controlling the number of turns and the revolving speed of the first motor 51 and the second motor 54.

The parameter input device is configured to configure coordinate information of an ablation region. In this embodiment, the parameter input device includes an ultrasonic probe for detecting a tissue boundary and an electrode position, and a touch screen for imaging.

The control device is in signal connection with the parameter input device and in control connection with the first motor 51 and the second motor 54 in the electrode driving device (in connection with the first motor 51 and the second motor 54 through a motor driving circuit). The control device respectively controls the displacement of the central electrode 11 and cylindrical electrode 13 according to preset coordinate information through the electrode driving device. In this embodiment, the control device includes an embedded computer, and various input and output devices connected with the embedded computer, the input devices include buttons (switches) and an ultrasonic probe, and the input and output device includes a touch screen.

When a discharging end of the electrode assembly 1 reaches a preset position, the control device controls the pulse waveform generator 2 to be connected with the electrode assembly 1.

When the electrode assembly 1 is connected with the pulse waveform generator 2, an ablation electric field is generated between the discharging end of the central electrode 11 and the cylindrical electrode 13, and the size (or radius) of the ablation electric field is positively correlated to the distance between the discharging end of the central electrode 11 and the cylindrical electrode 13.

The ablation electric field forms the ablation region after moving according to a preset path, and the ablation region is elliptical. In the moving process of the ablation electric field, the control device adjusts the size of the ablation electric field by changing the displacement difference between the cylindrical electrode 13 and the central electrode 11, such that the size (or radius) of the ablation electric field firstly changes from small to large and then changes from large to small.

Therefore, the selection of the ablation region decides the displacement of the two electrodes and the extreme values of the displacement difference in the moving process.

In order to simplify the operation, description is made by taking the ablation region is elliptical, so the coordinate information of the ablation region at least includes a long axis and a short axis for determining the size of the ablation region. In this embodiment, the long axis and the short axis are determined by clicking an image displayed on the touch screen.

The specific operation process of this embodiment is as follows:

1. The electrode assembly with suitable length and of suitable type is selected: the endoscope with the ultrasonic probe may be adopted, and then the electrode assembly is selected according to the target position (tumor tissues) detected by the ultrasonic probe.

2. The electrode assembly is mounted on an electrode driving device, and is connected with the pulse waveform generator 2 (which does not work at this moment) through the electrode wiring seat. In the mounting process, it should be guaranteed that the working section of the central electrode 11 is exposed out of the cylindrical electrode 13 and the cylindrical electrode 13 is not exposed out of the outer sheath tube 14, referring to FIG. 4. Then, the discharging end of the electrode assembly 1 is delivered to a position close to the target through the working channel of the endoscope, and the fixed part 31 is fixed with the endoscope (note: a suitable angle should be selected to guarantee that the part of the line on which the central electrode 11 is located overlaps the target for the largest length, this angle is determined by detecting the shape of the target in advance, and the selection of the angle does not involve the working principle of this embodiment, which is not described here in detail).

3. The length data of the long axis and the length data of the short axis are obtained by clicking the ultrasonic image boundary of the target on the touch screen.

4. The control device determines the position and size of the ablation region according to the length of the long axis and the short axis, and firstly controls the first motor 51 to start to make the central electrode 11 and the cylindrical electrode 13 to extend out of the outer sheath tube 14 at the same speed, until the central electrode 11 fully pierces the target and the cylindrical electrode 13 just reaches the boundary of the target.

Figure 8:
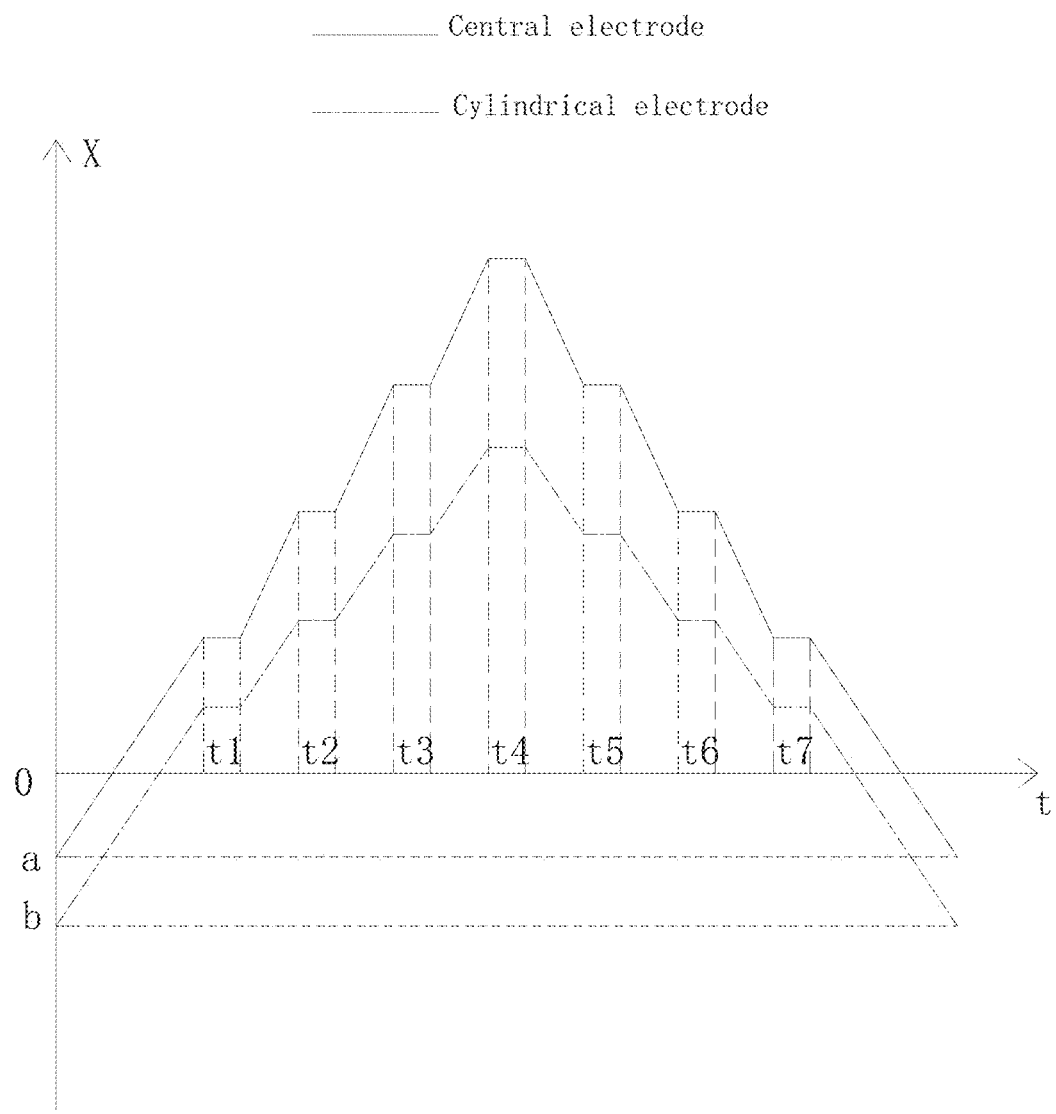
FIG. 8 illustrates a displacement change chart of a central electrode and a cylindrical electrode by taking an outer sheath tube (a tube mouth position is an origin) as a reference frame.

5. The control device controls the pulse waveform generator 2 to be connected with the electrodes, and the ablation electric field generated between the central electrode 11 and the cylindrical electrode 13 ablates the target and forms a first ablation layer; after the energy released by the ablation electric field in the first ablation layer reaches the preset value, the control device controls the first motor 51 and the second motor 54 to start synchronously, such that the central electrode 11 and the cylindrical electrode 13 enter a second ablation layer for ablation (since the second motor 54 is started in this process, the speed of the central electrode 11 is higher than the speed of the cylindrical electrode 13), and so forth until several ablation layers overlap (partially) to form the ablation region. In this process, the position statuses of the central electrode 11 and the cylindrical electrode 13 are as illustrated in FIGS. 5-8. FIG. 8 illustrates a displacement relationship of the central electrode 11 and the cylindrical electrode 13 by taking a tube mouth position of the outer sheath tube 14 as an origin during the formation of the ablation region. The electric field is released for ablation at seven periods of time, i.e., t1-t7.

In step 5, the ablation region is divided into several ablation layers in advance, so as to ensure that the energy released by the ablation electric field and received by each ablation layer in unit area (unit volume) is equal as far as possible, and is generally 80%-120% of the preset value.

The invention claimed is:

1. An electric pulse ablatograph for an endoscope, comprising: an electrode assembly comprising a central electrode and a cylindrical electrode and configured to pass through a working channel of the endoscope into a body and transmit a pulse to tissues in use;
    a pulse waveform generator coupled to the electrode assembly and configured to transmit pulse voltage to the electrode assembly;
    an electrode driving device configured to drive the central electrode and the cylindrical electrode;
    a parameter input device configured to configure coordinate information of an ablation region; and
    a control device in signal connection with the parameter input device and in control connection with the electrode driving device, wherein the control device respectively controls the displacement of the central electrode and cylindrical electrode according to preset coordinate information through the electrode driving device; when a discharging end of the electrode assembly reaches a preset position, the control device controls the pulse waveform generator to be connected with the electrode assembly;
    when the electrode assembly is connected with the pulse waveform generator, an ablation electric field is generated between the discharging end of the central electrode and the cylindrical electrode, and the size or radius of the ablation electric field is positively correlated to the distance between the discharging end of the central electrode and the cylindrical electrode;
    the ablation electric field forms the ablation region after moving according to a preset path, and the ablation region is elliptical;
    the electrode assembly is a layered structure, an outer side of the central electrode is plated with an insulating layer, and the part of the central electrode covered with the insulating layer is exposed out of the cylindrical electrode; the central electrode is retractably provided in the cylindrical electrode, and the cylindrical electrode is retractably provided in an outer sheath tube;
    the electrode driving device comprises a fixed part and a displacement part capable of producing a relative displacement, a first electric actuator provided on the fixed part and configured to drive the cylindrical electrode, and a second electric actuator provided on the displacement part and configured to drive the central electrode;
    the control device adjusts the size of the ablation electric field by changing the displacement difference between the cylindrical electrode and the central electrode.

2. The electric pulse ablatograph according to claim 1, wherein a front end of the fixed part is abutted with an inlet end of the working channel of the endoscope, the electrode assembly is placed in the working channel of the endoscope, a tail end of the outer sheath tube is fixedly connected with the fixed part, a tail end of the cylindrical electrode is fixedly connected with the displacement part, and the first electric actuator drives the displacement part to drive the cylindrical electrode to extend and retract in the outer sheath tube.

3. The electric pulse ablatograph according to claim 2, wherein the fixed part is in a needle tube shape, and a front end of the fixed part is provided with an interface for abutting the endoscope; the outer sheath tube is provided on the fixed part in a penetrating manner, one end of the outer sheath tube extends into the endoscope through the interface, and a tail end of the outer sheath tube and the fixed part are fastened through a cap in interference fit; the displacement part is cylindrical, sleeves the fixed part and is slidably provided relative to the fixed part in an axial direction; a tail end of the displacement part is provided with a cylindrical electrode tube seat for fixing the cylindrical electrode.

4. The electric pulse ablatograph according to claim 3, further comprising is a motor screw-nut mechanism and comprises a first motor, a screw and a nut; the first motor is fixedly provided on the fixed part, the nut sleeves the screw and is fixedly connected with the displacement part, and the first motor is in drive connection with the nut through the screw;
    the control device controls the extending and retraction displacement and speed of the cylindrical electrode in the outer sheath tube by controlling the number of turns and the revolving speed of the first motor.

5. The electric pulse ablatograph according to claim 3, further comprising is a linear motor and comprises a second motor and a push rod; the second motor is fixedly provided on the displacement part, the second motor is in drive connection with one end of the push rod, and the other end of the push rod is connected with the central electrode through a connector;
    the control device controls the extending and retraction displacement and speed of the central electrode in the cylindrical electrode by controlling the number of turns and the revolving speed of the second motor.

6. The electric pulse ablatograph according to claim 4, wherein the parameter input device comprises an ultrasonic probe for detecting a tissue boundary and an electrode position, and a touch screen for imaging; the coordinate information of the ablation region comprises a long axis and a short axis for determining the size of the ablation region, and the long axis and the short axis are determined by clicking an image on the touch screen.

7. The electric pulse ablatograph according to claim 1, wherein the central electrode comprises a working section at an end and a conducting section at a rear end for conducting voltage; during working, a pulse electric field is generated between the working section and the cylindrical electrode; the insulating layer is plated outside the conducting section.

8. The electric pulse ablatograph according to claim 7, wherein the central electrode is tubular and is hollow inside to form a medicine delivery channel for delivering medicine; a front end of the working section is provided with a sharp part.

9. The electric pulse ablatograph according to claim 5, wherein the parameter input device comprises an ultrasonic probe for detecting a tissue boundary and an electrode position, and a touch screen for imaging; the coordinate information of the ablation region comprises a long axis and a short axis for determining the size of the ablation region, and the long axis and the short axis are determined by clicking an image on the touch screen.

\* \* \* \* \*